(12) United States Patent
Nouvel

(10) Patent No.: US 8,293,286 B2
(45) Date of Patent: Oct. 23, 2012

(54) NATURAL COMPOSITIONS FOR KILLING PARASITES ON A COMPANION ANIMAL

(75) Inventor: Larry Nouvel, Plano, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 11/873,183

(22) Filed: Oct. 16, 2007

(65) Prior Publication Data
US 2008/0118585 A1  May 22, 2008

Related U.S. Application Data

(60) Provisional application No. 60/829,616, filed on Oct. 16, 2006.

(51) Int. Cl.
*A61K 36/00* (2006.01)
*A61K 36/53* (2006.01)

(52) U.S. Cl. .................. 424/725; 424/747

(58) Field of Classification Search .......... None
See application file for complete search history.

(56) References Cited

U.S. PATENT DOCUMENTS

| 4,374,853 | A | * | 2/1983 | Workman | 514/506 |
| 4,503,047 | A | * | 3/1985 | Bánfi et al. | 424/755 |
| 4,518,593 | A | | 5/1985 | Juvin et al. | |
| 5,439,690 | A | | 8/1995 | Knight | |
| 5,693,344 | A | | 12/1997 | Knight et al. | |
| 6,004,569 | A | | 12/1999 | Bessette et al. | |
| 6,114,384 | A | | 9/2000 | Bessette et al. | |
| 6,531,163 | B1 | | 3/2003 | Bessette et al. | |
| 2002/0156135 | A1 | | 10/2002 | Ninkov et al. | |
| 2004/0086540 | A1 | * | 5/2004 | Campbell et al. | 424/405 |
| 2005/0004233 | A1 | | 1/2005 | Bessette et al. | |
| 2005/0234119 | A1 | * | 10/2005 | Soll et al. | 514/406 |

FOREIGN PATENT DOCUMENTS

| DE | 202006001581 U1 | * | 5/2006 |
| EP | 1048293 A1 | * | 11/2000 |
| JP | 2001253806 A | * | 9/2001 |

OTHER PUBLICATIONS

Bar-Zeev et al, Laboratory evaluation of tick repellents, J. Med. Ent. 10 (1): 71-74, 1973.*
http://dog-health-website.blogspot.com/2005/05/flea-combs-flea-powdersand-other.html.
http://www.onlynaturalpet.com/products/Bite-This!-Flea-Remedy/119003.aspx , 2011.
http://grizzlybirds.blogspot.com/2006/07/green-cat-flee-fleas-integrated-pest.html.
Minimum Risk Products Exempted Under 40 CFR 152.25(f) Under the Authority of FIFRA 25(b), 1996.

* cited by examiner

*Primary Examiner* — Qiuwen Mi
(74) *Attorney, Agent, or Firm* — Polsinelli Shughart PC

(57) ABSTRACT

A method for killing parasites that includes topically applying onto a companion animal a composition including a natural, non-synthetic active ingredient. The composition may be applied to the animal in various forms, such as a spot-on, shampoo, an on animal spray, or an on animal powder. The present invention further relates to a topical composition for killing a parasite that includes at least one natural active ingredient.

18 Claims, No Drawings

NATURAL COMPOSITIONS FOR KILLING PARASITES ON A COMPANION ANIMAL

CROSS-REFERENCE TO RELATED APPLICATION

This application claims priority from Provisional Application Ser. No. 60/829,616 filed on Oct. 16, 2006, which is hereby incorporated by reference in its entirety.

FIELD OF THE INVENTION

The present invention relates to a method for killing parasites that includes topically applying onto a companion animal a composition including a natural, non-synthetic active ingredient. The composition may be applied to the animal in various forms, such as a spot-on, spray, powder, or shampoo.

BACKGROUND OF THE INVENTION

The infestation of animals with parasites is highly undesirable. Companion animals, for example, horses, dogs and cats all can serve as hosts for a large number of internal and external parasites. In companion animals, the presence of parasites can lead to discomfort, impaired health and performance, and even death. Each year, for example, millions of dogs and cats in the United States are treated for fleas, ticks, and mites. Flea, tick, and mite infestations cause great discomfort, transmit disease to pets and humans, and significantly interfere with the relationship between people and their pets. Societal changes have brought pets into the family home, intensifying the need for disease prevention.

Several classes of insecticides are effective for combating parasites. For example, pyrethroids, organophosphates, and organocarbamates are used to treat animals for parasite infestation. Various methods of formulating anti-parasitic agents are known in the art. These formulations include oral treatments, dietary supplements, powders, sprays, topical treatments (e.g., dips and pour ons), and shampoos. While each of these formulations has some efficacy in combating parasites, the formulations generally include synthetic insecticides. Synthetic insecticides, although effective, have been known to cause environmental effects that are harmful to humans and to the companion animal. Similarly, Pyrethrin, although extracted from the Chrysanthemum flower, is hard to process and standardize.

Natural insecticides, i.e., insecticides that include natural plant essential oils as an active ingredient, have been known to kill household parasites such as ants, cockroaches, and fleas by applying the natural insecticide in the form of a spray, powder, or liquid to a locus or area to be protected from the parasites, as disclosed in U.S. Pat. Nos. 5,439,690, 5,693,344, 6,114,384, and 6,531,163. In particular, the natural active ingredient in the insecticide has been included at a concentration of approximately 0.1% to 10% by weight of the insecticide. As such, a need still exists for methods and compositions to kill parasites on companion animals that include natural plant essential oils, have the same or higher efficacy level than synthetic insecticides, while still not harming or irritating the companion animal or its owner.

SUMMARY OF THE INVENTION

The present invention is directed to a method for killing parasites on a companion animal. The method includes topically applying onto the animal a composition including a natural, non-synthetic active ingredient.

The present invention is also directed to a method for killing parasites on a companion animal by applying onto the animal a spot-on composition or a shampoo composition. The spot-on composition may additionally include a solvent and the shampoo composition may additionally include a surfactant, a thickener, and an aqueous solvent.

The present invention is further directed to a method for killing parasites on a companion animal by applying an on animal spray composition or an on animal powder composition. The on animal spray composition may additionally include a solvent, and the on animal powder may additionally include a carrier, and absorbent ingredient.

DESCRIPTION OF THE PREFERRED EMBODIMENTS

In accordance with the present invention, a method for killing parasites on a companion animal has been discovered. The method includes topically applying onto the companion animal a composition including a natural, non-synthetic active ingredient. The composition may be applied to the animal in various forms, for example, but not limited to a spot-on, spray, powder, foam, or a shampoo. Advantageously, as the composition is natural it is safe to use on animals and safe to handle by their owners, and will not cause irritation to the skin of the companion animal or its owner.

I. Natural Active Ingredient

The composition of the present invention generally comprises at least one natural, non-synthetic, active ingredient (hereafter "active ingredient(s) refers to an active ingredient or active ingredient mixture that includes at least one natural active ingredient). In one embodiment, the active ingredient includes a plant essential oil. In another embodiment, the active ingredient can be one or more botanical extractives. The term "plant essential oil," as used herein, refers to a monocyclic, carbocyclic ring structure having six-members and substituted by at least one oxygenated or hydroxyl functional moiety. Suitable plant essential oils include, but are not limited to, members selected from the group consisting of peppermint oil, cinnamon leaf oil, lemongrass oil, clove oil, castor oil, wintergreen oil, aldehyde C16 (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol (cineole), eugenol, iso-eugenol, galaxolide, geraniol, guaiacol, ionone, menthol, methyl salicylate, methyl anthranilate, methyl ionone, methyl salicylate, a-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, ethyl vanillin, similar compositions, and combinations thereof. These plant essential oil compounds are known and used to control insects in a locus or area to be protected from the parasites, as described by U.S. Pat. Nos. 5,439,690, 5,693,344, 6,114,384, and 6,531,163, the entire contents of which are incorporated by reference herein for all relevant purposes. In addition, the active ingredient may be commercially purchased from EcoSmart, Inc. (Atlanta, Ga.). Although these ingredients have been used to control insects in an area, such bedding for the companions animal or the companion animal's owners furniture and living area, in the form of a spray, powder, or liquid, as disclosed in U.S. Pat. Nos. 5,439,690, 5,693,344, 6,114,384, and 6,531,163, these ingredients were only used at a concentration of approximately 0.1% to 10% by weight of the insecticide. As such, the use of this natural active ingredient for killing parasites on a companion animal at higher dosages, without causing irritation or harm to the companion animal or its owner, has been discovered.

In one embodiment, the active ingredient includes a mixture of peppermint oil, cinnamon leaf oil, lemongrass oil, eugenol, and thyme oil. The active ingredient may additionally include 2-phenyl ethyl propionate. The active ingredient may also be a combination of two or more plant essential oils. The concentration of the active ingredient can and will vary depending on its desired application. In one embodiment, the active ingredient comprises from about 0.1% to about 25% by weight of the composition. Additionally, the active ingredient comprises from about 10% to about 25% by weight of the composition.

Additionally, an amount of a synthetic active ingredient may be mixed with the natural active ingredient to form an active ingredient mixture. The synthetic active ingredient can be any insecticide used in the industry for combating parasites including but not limited to, pyrethroids (e.g., cypermethrin, imiprothrin, lambda cyhalothrin, permethrin, chlorpyrifos, phenothrin, diazinon, etofenprox, and pyrethrins (e.g., pyrethin I, pyrethrin II, cinevin I, cinevin II, jasmolin I, and jasmolin II)), N-phenylpyrazole derivatives (i.e., fipronil), organophosphates or organocarbamates (e.g., dichlorvos, cythioate, diazinon, malathion, carbaryl, fenthione, methylcarbamate, and prolate), imidacloprid, arylheterocycles, insect growth regulators (e.g., agridyne, diofenolan, fenoxycarb, hydroprene, kinoprene, methoprene, pyriproxyfen, tetrahydroazadirachtin, chlorfluazuron, cyromazine, diflubenzuron, fluazuron, flucycloxuron, flufenoxuron, hexaflumuron, ifenuron, tebufenozide, and triflumuron), amitraz, selamectin, nitenpyram and combinations thereof.

The active ingredient neurally affects parasites killing them. The parasite is typically an ectoparasite, such as a flea, tick, lice, mosquito, or ear mite. These parasites have an exoskeleton, cuticle, or outer shell that has an outer waxy coating. This thin shell and the waxy coating is the primary protection the insect has to insure the maintenance of its vital body fluids. If an insect loses as little as 10% of these fluids, it will die. The exoskeleton provides protection against most foreign agents such as pesticidal liquids and powders.

The active ingredient is a neurally effective chemical that is capable of dissolving or in some way penetrating the cuticle or waxy coated exoskeleton of a parasite such that the chemical interacts or binds with a vital substance within the parasite thereby killing it. The active ingredient is also believed to target and block a key neurotransmitter receptor site called octopamine, which is found in all invertebrates but not mammals. Because octopamine regulates an insect's heart rate, movement, behavior and metabolism, this unique mode-of-action results in a total breakdown of the insect's nervous system.

II. Animal Spot-On

The composition of the present invention may be used as an animal spot-on composition to kill parasites on a companion animal. The method of treating the animal includes topically applying the spot-on composition including an active ingredient to the animal.

The animal spot-on composition includes an active ingredient and a solvent. The active ingredient is as described in Part I above. The solvent may be added to change the solubility characteristics of the active ingredient so as to increase or decrease the release rate of the active ingredient as the composition is sprayed. The solvent may be selected from any solvents for oils known in the art suitable for contact with skin, causing none or minimal irritation. Examples of suitable solvents include, but are not limited to, alcohols such as isopropyl myristate, isopropyl alcohol, butyl myristate, and combinations thereof. In another embodiment, the animal spot-on composition may include an odor-masking agent. The odor-masking agent may be any component that masks the odor of the solvent, examples include, but are not limited to vanillin, methyl vanillin, ethyl vanillin, almond oil, rose oil, or any other natural extractives or synthetic ingredients used for odor-masking. Additionally, the animal spot-on composition may also include a synthetic or non-natural active ingredient in combination with the natural, or plant essential oil active ingredient. Suitable synthetic active ingredients that may be included in the spot-on composition include pyrethroids (e.g., cypermethrin, imiprothrin, lambda cyhalothrin, permethrin, chlorpyrifos, phenothrin, diazinon, etofenprox, and pyrethrins (e.g., pyrethin I, pyrethrin II, cinevin I, cinevin II, jasmolin I, and jasmolin II)), N-phenylpyrazole derivatives (i.e., fipronil), organophosphates or organocarbamates (e.g., dichlorvos, cythioate, diazinon, malathion, carbaryl, fenthione, methylcarbamate, and prolate), imidacloprid, arylheterocycles, insect growth regulators (e.g., agridyne, diofenolan, fenoxycarb, hydroprene, kinoprene, methoprene, pyriproxyfen, tetrahydroazadirachtin, chlorfluazuron, cyromazine, diflubenzuron, fluazuron, flucycloxuron, flufenoxuron, hexaflumuron, ifenuron, tebufenozide, and triflumuron), amitraz, selamectin, and nitenpyram.

The animal spot-on composition may comprises from about 10% to about 25% by weight of the active ingredient and from about 75 to about 80% by weight of the solvent. The animal spot-on composition can include from about 1% to about 4% by weight peppermint oil, from about 1% to about 5% by weight cinnamon leaf oil, from about 1% to about 5% by weight lemongrass oil, from about 1% to about 6% by weight eugenol, from about 1% to about 6% by weight thyme oil, and from about 80% to about 95% by weight isopropyl myristate. In a further example, the animal spot-on composition further comprises from about 1% to about 6% by weight 2-phenyl ethyl propionate. Additionally, the animal spot-on composition further comprises from about 0.1 to about 2% by weight vanillin.

III. Animal Shampoo

The composition of the present invention may also be used as an animal shampoo composition to kill parasites on a companion animal. The method of treating the animal includes topically applying the shampoo composition including an active ingredient to the animal.

The animal shampoo composition includes an active ingredient, an aqueous solvent, and a surfactant. The active ingredient is as described in Part I above. The solvent is as described in Part II. In another embodiment, the animal shampoo composition may also include a synthetic or non-natural active ingredient in combination with the natural, or plant essential oil active ingredient as described in Part I above. Suitable synthetic active ingredients that may be included in the shampoo composition include pyrethroids (e.g., cypermethrin, imiprothrin, lambda cyhalothrin, permethrin, chlorpyrifos, phenothrin, diazinon, etofenprox, and pyrethrins (e.g., pyrethin I, pyrethrin II, cinevin I, cinevin II, jasmolin I, and jasmolin II)), N-phenylpyrazole derivatives (i.e., fipronil), organophosphates or organocarbamates (e.g., dichlorvos, cythioate, diazinon, malathion, carbaryl, fenthione, methylcarbamate, and prolate), imidacloprid, arylheterocycles, insect growth regulators (e.g., agridyne, diofenolan, fenoxycarb, hydroprene, kinoprene, methoprene, pyriproxyfen, tetrahydroazadirachtin, chlorfluazuron, cyromazine, diflubenzuron, fluazuron, flucycloxuron, flufenoxuron, hexaflumuron, ifenuron, tebufenozide, and triflumuron), amitraz, selamectin, and nitenpyram.

The animal shampoo composition of the invention comprises at least one surfactant, which may be selected from anionic, nonionic, amphoteric and zwitterionic surfactants and mixtures thereof. Additionally, any surfactant known in the industry can be utilized.

The composition may further include other ingredients such as, but not limited to, other types of surfactants (semi-polar or nonionic) rheology modifiers, coloring agents, protein derivatives, fragrance, and vitamins.

Examples of suitable anionic surfactants include, but are not limited to, alkyl sulfates, alkyl ether sulfates, alkaryl sulfonates, alkyl sulfosuccinates, n-alkyl sarcosinates, alkyl phosphates, alkyl ether phosphates, alkyl ether carboxylates and alpha-olefin sulfonates, especially their ammonium, sodium, magnesium and mono-, di- and triethanolamine salts. As an example the alkyl groups generally contain from 8 to 18 carbon atoms and may be saturated or unsaturated. The alkyl ether sulfates, alkyl ether phosphates and alkyl ether carboxylates may contain from 1 to 10 ethylene oxide units per molecule. In a further example, one particular group of anionic surfactants are members selected from the group consisting of sodium lauryl sulfate, sodium laureth sulfate, ammonium lauryl sulfate, ammonium laureth sulfate, disodium laureth sulfosuccinate; disodium ricinoleamido monoethanolamide ("MEA") sulfosuccinate, sodium cocoyl isethionate, sodium methyl oleoyl taurate, sodium methyl cocoyl taurate, sodium laureth-13 carboxylate, sodium C14-16 olefin sulfonate, sodium laureth-4 phosphate, laureth-3 phosphate, triethylanolamine lauryl sulfate, magnesium lauryl sulfate, sodium tridecyl sulfate, and alpha-olefin sulfate. Another specific group includes ammonium laureth sulfate, ammonium lauryl sulfosuccinate, and triethanolamine lauryl sulfate.

Suitable amphoteric surfactants are those selected from the group consisting of sultaines (such as cocamidopropyl hydroxy sultaine); glycinates (such as cocoamphocarboxyglycinates); glycines (such as cocoamidopropyldimethylglycine); propionates (such as sodium lauriminodipropionate, sodium cocamphopropionate, disodium cocoamphodipropionate, and cocoamphocarboxypropionate). In addition, Psuedo amphoteric (ampholytic) surfactants such as betaines are also commonly grouped within the designation-Amphoteric surfactants and can be used for similar purposes. Useful betaines include cocamidopropyl, coco, and oleamidopropyl.

Nonionic surfactants suitable for use in the composition of the invention may include condensation products of aliphatic (C8-18) primary or secondary linear branched chain alcohols with alkylene oxides or phenols with alkylene oxides, usually ethylene oxide and generally having from 6 to 30 ethylene oxide groups. Nonionic surfactants suitable for use in the compositions of the present invention can include fatty acid alkanolamides. Representative fatty acid alkanolamides include those having C10-C18 carbons. For example, fatty acid diethanolamides such as isostearic acid diethanolamide and coconut fatty acid diethanolamide. Suitable fatty acid monoethanolamides, which may be used, include coconut fatty acid monoethanolamide and coco mono-isopropanolamide.

Semi-polar surfactants such as amine oxides are also suitable for use in the present invention. These include N-alkyl amine oxide, and N-stearyl dimethylamine oxide. A suitable N-acyl amide oxide includes N-cocamidopropyl dimethylamine oxide. The hydrophobic portion of the amine oxide surfactant may be provided by a fatty hydrocarbon chain having from about 10-21 carbon atoms. In an exemplary embodiment, the surfactant may be Pluronic L92 or Pluronic L81 commercially purchased from BASF.

While not required, the shampoo composition may contain thickeners to retard the settling process by increasing the viscosity of the composition. By way of example, thickeners may be utilized to increase the viscosity of the composition. Suitable thickening agents include, but are not limited to, water-soluble, guar- or xanthan-based gums, cellulose ethers, modified cellulosics and polymer, and microcrystalline cellulose anti-packing agents. For example, a thickening agent may be an ethoxylated methyl glucose ether, commercially purchased as Glucamate® LT from Noveon, Inc, among others.

Similarly, while not required, a preservative may alternatively be added to the shampoo composition to prevent germs from forming. Suitable preservatives include sodium benzoate, parabens, DMDM hydantoin, tetrasodium EDTA, and chloroallylhexaminium chloride, commercially purchased as Dowicil® from Dow Chemical Company, among others.

The animal shampoo composition comprises from about 10% to about 25% by weight of the active ingredient, from about 50% to about 80% by weight of the aqueous solvent, and from about 15% to about 35% by weight surfactant. In another embodiment, the animal shampoo composition comprises from about 0.1% to about 5% by weight peppermint oil, from about 0.5% to about 5% by weight cinnamon leaf oil, from about 0.5% to about 5% by weight lemongrass oil, from about 0.5% to about 5% by weight eugenol, and from about 0.5% to about 5% by weight thyme oil, from about 50% to about 70% by weight water, from about 0.01% to about 1% by weight preservative, from about 0.5% to about 3% by weight thickener. Additionally, the animal shampoo composition further comprises from about 3% to about 4% by weight 2-phenyl ethyl propionate.

IV. Animal Spray

The composition of the present invention may also be used as an on animal spray composition to kill parasites on a companion animal. The method of treating the animal includes topically applying the spray composition including an active ingredient to the animal.

The animal spray composition typically includes an active ingredient and a solvent. The active ingredient is as described in Part I above. The solvent is as described in Part II above. In one embodiment, the active ingredient is a mixture comprising peppermint oil, cinnamon leaf oil, lemongrass oil, eugenol, thyme oil, and vanillin. Additionally, the active ingredient mixture includes an amount of 2-phenyl ethyl propionate.

The animal spray composition comprises from about 0.1% to about 20% by weight of the active ingredient and from about 80% to about 99.8% by weight of the solvent. The animal spray composition may include, for example, from about 0.5% to about 2% by weight peppermint oil, from about 1% to about 2% by weight cinnamon leaf oil, from about 1% to about 2% by weight lemongrass oil, from about 1.5% to about 2% by weight eugenol, from about 1.5% to about 2% by weight thyme oil, from about 0.1 to about 1% by weight vanillin, and from about 85% to about 95% by weight of isopropyl myristate, isopropyl alcohol, or combinations thereof. Additionally, the animal spray composition further comprises from about 1.5% to about 2% by weight 2-phenyl ethyl propionate.

V. Animal Powder

The composition of the present invention may also be used as an on animal powder composition to kill parasites on a companion animal. The method of treating the animal includes topically applying the powder composition including an active ingredient to the animal.

The animal powder composition typically includes an active ingredient, an absorbent, and a carrier. The active ingredient is as described in Part I above. The carrier mechanically punctures the exoskeleton of the parasite and accelerates the interaction between the active ingredient and the vital substance within the parasite. The absorbent is typically a dehydrating agent, which provides another mode for killing the parasite. Examples of suitable carriers include, but are not limited to, sodium bicarbonate, calcium carbonate, and combinations thereof. Suitable absorbents include alkali silica compounds, such as Microcel E, commercially available from World Minerals.

The effectiveness of the powder composition is probably the result of an interaction between one or more of the carriers and/or absorbent and the active ingredient, rather than from desiccation per se. Once deposited on an insect, some powders create a "water continuum" between the inside and outside of the insect. Hemolymph, in the form of lipid-water liquid crystals, is drawn by the powder to the surface from the interior of the insect through microscopic wax canals in the cuticle. Substances carried in the powder may then pass through the continuum into the insect where they come in contact with nerves bathed by the hemolymph. This process may occur very rapidly. Another possibility of action is that the powder components facilitate rapid penetration of an active substance through the cuticle. Oily and alcoholic substances such as the neurally effective substance reported herein may readily penetrate thin or untanned portions of cuticle.

The animal powder composition comprises from about 0.1% to about 10% by weight of the active ingredient, from about 40% to about 60% by weight of the absorbent, and from about 30 to about 50% by weight of the carrier. The animal powder composition may include, for example, from about 0.5% to about 2% by weight peppermint oil, from about 1.5% to about 2% by weight cinnamon leaf oil, from about 1.5% to about 2% by weight lemongrass oil, from about 1.5% to about 2.5% by weight eugenol, from about 1.5% to about 2.5% by weight thyme oil, from about 0.1 to about 1% by weight vanillin, from about 40% to about 60% by weight alkali silicate, from about 10% to about 20% by weight sodium bicarbonate, and from about 10% to about 20% by weight calcium carbonate. Additionally, the animal powder composition further comprises from about 1.5% to about 2% by weight 2-phenyl ethyl propionate.

VI. Treatment of Animals Against Parasites

The compositions disclosed herein (i.e., on animal spray, on animal powder, spot-on, and shampoo) are useful as topical anti-parasitic agents. In one example, the composition may be applied topically to an animal in an effective amount to kill the varieties of parasites and pests for which the composition has been selected. The compositions of the invention may be used on a variety of companion animals including, but not limited to, dogs, cats, and horses.

Each composition of the invention may be applied topically to an animal according to practices known to those skilled in the art. For example, the spot-on composition may be applied to any of a variety of spots on the animal's skin. In another example, the composition may be applied between the two shoulders of the animal.

Administration of each composition may be intermittent in time and may be administered daily, weekly, biweekly, monthly, bimonthly, or even for longer durations of time. The time period between treatments depends upon factors such as the parasite(s) or pests being treated, the degree of infestation, the type of companion animal and the environment where it resides. It is well within the skill level of the practitioner to determine a specific administration period for a particular situation. For example, the treatment for dogs and cats is on a biweekly or monthly basis for a spot-on composition.

The effective amount of each composition to be applied to an animal is dependent upon the identity of the active ingredient, the type of composition (i.e., spray, powder, spot-on, or shampoo), the animal species to be treated, and environmental conditions. For example, a dose of the spot-on composition may range from about 0.01 to about 1000 mg per kg of the animal's body weight. The shampoo composition is typically applied on the animal at a dosage sufficient to lather the coat of the animal. But the amount may vary by an order of magnitude or more in some instances without departing from the scope of the invention.

In another embodiment, the active ingredients of the present invention may also be incorporated into an animal collar to be worn by the companion animal, a toilette or animal wipe to be rubbed onto the animal's coat, or as a mousse to be applied onto the animal's coat. In another embodiment, the active ingredient of the present invention may also be incorporated into an ear mite composition to kill ear mites.

The following examples are simply intended to further illustrate and explain the present invention. The invention, therefore, should not be limited to any of the details in these examples.

Definitions

The term "companion animal" as used herein refers to an animal kept for companionship or enjoyment.

The term "solvent" as used herein refers to a liquid that dissolves any liquid, solid, or gas resulting in a solution. The "solvent" as used herein is further suitable for contact with skin, resulting in none to minimal irritation.

The term "parasite" as used herein refers to an organism that lives in or on a second organism.

The term "pest" as used herein refers to an organism that causes harm, damage, or discomfort to a companion animal.

The term "synthetic" used herein refers to an artificial product made by chemical synthesis.

The term "topical" used herein refers to a topical medicine or topical treatment that is applied to a body surface, such as the skin or mucus membranes, of the companion animal.

EXAMPLES

Examples 1-6 illustrate various embodiments of the invention

Example 1

Use of Dog Spot-on Compositions to Determine Efficacy Against Fleas, Ticks and Mosquitoes To determine the efficacy of the spot-on composition and method of use for the present invention an amount of the spot-on composition was used to treat a test group of dogs and puppies and compared to the control group of dogs and puppies that were not treated.

Twelve dogs were selected for the current test. The twelve dogs were selected randomly, with varying breeds, sex, hair length, age, and weight (under 15 lbs). Prior to the test, the dogs were exposed to fleas and ticks to ensure infestation would occur. This pre-test evaluation/acclimation period ensures the test dogs ability to hold a viable population of fleas and ticks. Prior to the current test, the dogs were thoroughly combed to remove any residual fleas or ticks.

All twelve dogs were infested with 100 unfed adult fleas (*Ctenocephalides felis*) and 50 unfed adult ticks (*Rhipicephalus sanguineaus* and/or *Dermacentor variabillis*) on test day −1 (one day prior to day 0, which is the initial treatment day). The test dogs were divided into two groups, Group A the control group and the treated Group D (treated with the spot-on composition). On day 0 each dog in Group D is treated with a 2 ml dose of the spot-on composition. The spot-on formulation is provided in Table 1. Dogs in Group A were the control and receive no spot-on composition.

Dogs in Group D were treated with the spot-on composition on day 0 and day 6. Group D was the further divided into two sub groups with alternating sub groups receiving treatment on day 14, day 20 and day 27. During the testing period re-infestation may be required and is scheduled for the day after treatment, day 7, day 15, day 21, and day 28.

On day 3, day 9, day 16, day 27, and day 37 the number of fleas and ticks on the dogs were calculated. Hand counts were preformed to determine the number of fleas and ticks respectively. The hand counts were conducted in accordance with Sharp Veterinary Research SOP #14-0 for fleas and SOP # 13-0 for ticks. The efficacy values were then calculated as percentage reduction from the control group count. Group efficacy values were calculated from the aggregate of the individual efficacy values.

Efficacy against fleas was variable with a range of 0% to 86%. The average efficacy for Group D on the days listed above (3, 9, 16, 27, and 37) ranged from 53% to 70%. Efficacy against fleas tended to be higher in the week immediately after each treatment. The statistical analyses of the Group D dogs (treated) versus the Group A dogs (control) demonstrates that the flea count, and therefore the infestation, in the Group D dogs were significantly lower than the Group A dogs. Therefore the spot-on composition demonstrates a high efficacy against the fleas, with the treated dogs in Group D demonstrating a significantly lower burden of fleas than when compared to the control dogs, Group A.

The average efficacy for Group D against ticks on the days listed above range from 65% to 95% with the 65% corresponding to day 37. Typically, efficacy against the ticks was consistently high (80% to 100%) throughout each two-week period after treatment. The statistical analyses of the Group D dogs (treated) versus the Group A dogs (control) demonstrates that the tick count, and therefore infestation, in the Group D dogs were significantly lower than the Group A dogs. Therefore, the spot-on composition demonstrates a high efficacy against the ticks, with the treated dogs in Group D demonstrating a significantly lower burden of ticks when compared to the control dogs, Group A.

The dogs were also tested for mosquito contacts. In the mosquito test conducted on day zero, soon after application of the compositions, there was evidence in the dogs of Group D that the composition provided some vapor repellent action since, compare with untreated dogs, 43% fewer mosquitoes landed on these dogs in the first 5 minutes after exposure. There was substantial evidence in 2 of the 3 treated dogs that treatment with both compositions effectively (100%) inhibited hungry *Aedes aegypti* female mosquitoes from taking a blood meal. In the second mosquito test, conducted 27 days after treatment, there was no evidence of vapor repellency shown in the counts of mosquito landings in the first 5 minutes after exposure. In both groups of treated dogs, one of the three treated dogs was protected (at 100%) against feeding by hungry female mosquitoes. There were no significant differences between any of the values derived from the mosquito study after the initial exposure to the spot-on composition.

TABLE 1

Composition for Dog Spot-on Composition

| Ingredient | Amount |
| --- | --- |
| Peppermint oil | 3.00% |
| Cinnamon leaf oil | 4.50% |
| Clove Oil | 5.00% |
| Thyme Oil | 5.00% |
| Isopropyl Myristate | 76.50% |
| Vanillin | 1.50% |

Example 2

Efficacy of Cat Spot-on Compositions vs. Synthetic Spot-on Composition

Two spot-on compositions were applied to a group of cats at a mean dose rate of 2 ml per cat. Three cats were untreated controls (Group I) and six cats, in two groups, each of 3, were treated once with each composition on day zero. The cats in Group II were treated with the cat spot-on composition and the three cats in Group III were treated with a synthetic spot-on composition. The flea and tick infestation was then monitored and calculated. Efficacy was calculated as described in Example 1.

All the cats were infested with fleas as previously described in Example 1 or through exposure of the cats to a controlled environment that contains fleas. Exposure through this controlled environment mimics the natural situation that pets encounter causing infestation or contact of common pests, such as fleas, ticks, and mosquitoes. Either exposure procedure causes the animal to become infested or come in contact with the pests, such as fleas, ticks, and mosquitoes.

Efficacy against new fleas, applied on the day after treatment, was absolute for both test substances at 100% on day 2. Thereafter, efficacy of the cat spot-on composition declined compared with the synthetic spot-on composition product. Efficacy of the synthetic spot-on composition remained high for the first 2 weeks but declined progressively during the third and fourth weeks. Although efficacy of the cat spot-on composition was reduced, values exceeding 70% reduction in flea burdens (compared with the untreated controls) were maintained until re-treatment at 14 days and thereafter for the following 3 weeks. Statistical analyses of apparent differences in flea counts between the untreated controls and the treated cats showed that throughout the 35 days of the study flea burdens on all the treated cats were consistently smaller than on the untreated controls. The flea burdens on the spot-on composition cats were higher than on the cats treated with the synthetic spot-on product on days 7 through 11. In contrast, after re-treatment of the cats with the cat spot-on composition on day 14 the flea burdens on the spot-on composition cats were uniformly significantly lower than those on the synthetic spot-on composition cats. The hair coats of the treated cats were examined for adverse cosmetic effects; none were demonstrated for the spot-on composition.

The data indicate that the cat spot-on composition is efficacious in limiting flea burdens on cats exposed to repeated low-grade flea challenge for at least 3 weeks after treatment. The synthetic spot-on composition (dose rate of etofenprox in the range of 217 to 285 mg/kg) performed as seen in its pre-registration evaluations for at least 2 weeks but declined thereafter below the label claim ("up to 4 weeks residual efficacy").

TABLE 2

Composition for Cat Spot-On Composition

| Ingredient | Amount |
|---|---|
| Peppermint oil | 3.00% |
| Cinnamon leaf oil | 4.50% |
| Clove Oil | 5.00% |
| Thyme Oil | 5.00% |
| Solvent | 76.50% |
| Vanillin | 1.50% |

Example 3

Efficacy of Cat Spot-on Compositions vs. Synthetic Spot-on Composition

Two spot-on compositions, as described in Example 2, were applied to a group of cats at a dose rate of 0.75 ml per cat. Three cats were untreated controls (Group I) and six cats, in two groups, each of 3, were treated once with each composition on day zero. The cats in Group II were treated with the cat spot-on composition and the three cats in Group III were treated with a synthetic spot-on composition. The flea and tick infestation was then monitored and calculated. Efficacy was calculated as described in Example 1.

All the cats were infested with fleas as previously described in Example 2.

The mean group efficacy against fleas, applied on the day after treatment was 50% for the synthetic spot-on and 68% for the cat spot-on composition. The best individual efficacy value of the synthetic spot-on was 75% while 2 of the 3 cats treated with the spot-on composition had efficacy values of 86% and 100%. Thereafter, efficacy values for the synthetic spot-on declined steadily to below 50% over the next 2 weeks with most values being in the range of 30% to zero. The mean group efficacy values against fleas for the cat spot-on composition also declined, but less precipitously, with individual values over 50% for up to 3 weeks. Efficacy against ticks was substantially higher than against flees, particularly for the cat spot-on composition, which was effective at 100% for almost one week. However, as with the flea results, the synthetic spot-on composition was substantially less efficacious against ticks with most efficacy values over the first week being less than 60% and no treated cats were free of ticks at any time. The efficacy of the synthetic spot-on against ticks continued to decline with mean group efficacy values being below 50% to less than 20% over the following 2½ weeks. Although the individual and mean group efficacy values against ticks achieved by the cat spot-on product also declined and varied from day to day, individual treated cats were still found to be free of ticks through the third week after treatment.

Statistical analyses of apparent differences in flea counts between the untreated controls and the treated cats showed that while the flea and tick burdens on the cats treated with the synthetic spot-on were significantly lower than those of the untreated controls on only 3 out of 28 counts, there were statistically fewer fleas and ticks on the cats treated with the cat spot-on composition for more than half of the counts. The apparent differences in the numbers of fleas and ticks between the cats treated with these two test substances were statistically significant for 10 of the counts and the numbers of parasites on the cats treated with the synthetic spot-on composition were, with few exceptions, always higher than on the cats that had been treated with the cat spot-on composition.

Example 4

Efficacy of Flea Spray Compositions for Dogs (on Animal Spray)

To determine the efficacy of a liquid spray composition an amount of the liquid spray composition was used to treat a test group of dogs and puppies, and compared to the control group of dogs and puppies not treated.

As previously outlined in Example 1, two groups of dogs were selected. Group A was the control and Group B were the dogs treated with the spray composition. The spray composition is provided in Table 3 below.

All the dogs were infested with fleas as previously described in Example 1 or through exposure of the dogs to a controlled environment that contains fleas. Exposure through this controlled environment mimics the natural situation that pets encounter causing infestation or contact of common pests, such as fleas, ticks, and mosquitoes. Either exposure procedure causes the animal to become infested or come in contact with the pests, such as fleas, ticks, and mosquitoes.

After exposure and infestation of the fleas to dogs in Group A and B, treatment commenced. Group A, or the control group received no treatment. Group B, received an amount of the spray composition at a dose rate of 3.7 g per kg. body weight. The spray composition was further administered to the Group B dogs on day 0 and day 14. The efficacy of the spray composition was then measured over 17 days following the first treatment. The efficacy was calculated as described in Example 1.

Efficacy against fleas was variable with a range of 62% to 100% for up to four days after the treatment. After this initial four-day period the efficacy is less substantial when compared to the control. The efficacy results demonstrate that the spray composition is effective in limiting flea burden on dogs exposed to repeated exposure for up to four days after treatment. Therefore, the spray composition demonstrated a high efficacy against the fleas, with the treated dogs in Group B demonstrating a significantly lower burden than when compared to the control dogs, Group A.

TABLE 3

Composition for Dog Spray Composition

| Ingredient | Amount |
|---|---|
| Peppermint oil | 1.00% |
| Cinnamon leaf oil | 1.50% |
| Lemongrass oil | 1.50% |
| Vanillin | 0.50% |
| Eugenol | 1.70% |
| Thyme Oil | 1.70% |
| IPA | 40.00% |
| Solvent | 76.50% |

Example 5

Efficacy of Flea Powder Compositions for Dogs (on Animal Powder)

To determine the efficacy of a powder composition an amount of the powder composition was used to treat a test group of dogs and puppies, and compared to the control group of dogs and puppies not treated.

As previously outlined in Example 1, two groups of dogs were selected. Group A was the control and Group B were the dogs treated with the powder composition. The powder composition is provided in Table 4 below.

All the dogs were infested with fleas as previously described in Example 4.

After exposure and infestation of the fleas to dogs in Group A and B, treatment commenced. Group A, or the control group received no treatment. Group B, received an amount of the powder composition at a dose rate of 2.0 or 3.7 g per kg. body weight. The powder composition was administered to the Group B dogs on day 0. The efficacy of the powder composition was then measured over 14 days following the treatment on day 0. The efficacy was calculated as described in Example 1.

Efficacy against fleas were variable but demonstrated a 50% efficacy throughout the 14 day study. The efficacy results demonstrate that the powder composition is effective in limiting flea burden on dogs exposed to repeated exposure for up to 14 days after treatment. Therefore, the powder composition demonstrated a high efficacy against the fleas, with the treated dogs in Group B demonstrating a significantly lower burden than when compared to the control dogs, Group A.

TABLE 4

Composition for Dog Powder Composition

| Ingredient | Amount |
| --- | --- |
| Peppermint oil | 1.20% |
| Cinnamon leaf oil | 1.80% |
| Lemongrass oil | 1.80% |
| Vanillin | 0.60% |
| Eugenol | 2.10% |
| Thyme Oil | 2.10% |
| Microcel E | 51.60% |
| Calcium carbonate | 19.40% |
| Sodium bicarbonate | 19.40% |

Example 6

Efficacy of Flea Powder Compositions for Cats (on Animal Powder)

To determine the efficacy of a powder composition an amount of the powder composition was used to treat a test group of cats and kittens, and compared to the control group of cats and kittens not treated.

As previously outlined in Example 1, two groups of dogs were selected. Group A was the control and Group B were the dogs treated with the powder composition. Example 5 changes the test subjects to cats, but the remainder of the protocol remains the same as outlined in Example 1. The powder composition is provided in Table 4 below.

All the cats were infested with fleas as previously described in Example 4, except cats were the test subjects not dogs.

After exposure and infestation of the fleas to cats in Group A and B, treatment commenced. Group A, or the control group received no treatment. Group B, received an amount of the powder composition at a dose rate of 2.0 or 3.7 g per kg. body weight. The powder composition was further administered to the Group B cats on day 0. The efficacy of the powder composition was then measured over 14 days following the treatment on day 0. The efficacy was calculated as described in Example 1.

Efficacy against fleas were variable but demonstrated a 50% efficacy throughout the 14 day study. The efficacy results demonstrate that the powder composition is effective in limiting flea burden on cats exposed to repeated exposure for up to 14 days after treatment. Therefore, the powder composition demonstrated a high efficacy against the fleas, with the treated cats in Group B demonstrating a significantly lower burden than when compared to the control cats, Group A.

TABLE 4

Composition for Cat Powder Composition

| Ingredient | Amount |
| --- | --- |
| Peppermint oil | 1.20% |
| Cinnamon leaf oil | 1.80% |
| Lemongrass oil | 1.80% |
| Vanillin | 0.60% |
| Eugenol | 2.10% |
| Thyme Oil | 2.10% |
| Microcel E | 51.60% |
| Calcium carbonate | 19.40% |
| Sodium bicarbonate | 19.40% |

While the invention has been explained in relation to exemplary embodiments, it is to be understood that various modifications thereof will become apparent to those skilled in the art upon reading the description. Therefore, it is to be understood that the invention disclosed herein is intended to cover such modifications as fall within the scope of the following claims.

What is claimed is:

1. A method for reducing the incidence of infestation of a parasite on a companion animal and killing a parasite in combination, the method comprising topically applying to a companion animal a composition comprising an active ingredient, wherein the active ingredient consists of methyl salicylate, thymol, vanillin, and lemon grass oil.

2. The method of claim 1, wherein the active ingredient is present in an amount of from about 2.5% to about 25% by weight.

3. The method of claim 1, wherein the composition further comprises at least one solvent.

4. The method of claim 3, wherein the solvent is selected from the group consisting of isopropyl myristate, isopropyl alcohol, butyl myristate, and combinations thereof; and
wherein the solvent comprises from about 75% to about 99% by weight of the composition.

5. The method of claim 1, wherein the composition further comprises an odor modifying ingredient.

6. The method of claim 1, wherein the composition further comprises an absorbent.

7. The method of claim 1, wherein the composition further comprises a carrier.

8. The method of claim 7, wherein the carrier is selected from the group consisting of sodium bicarbonate, calcium carbonate, and combinations thereof; and wherein the carrier comprises from about 30% to about 50% by weight of the composition.

9. The method of claim 1, wherein the composition is selected from the group consisting of a spot-on, a shampoo, an on animal spray, an on animal powder, a foam, an animal collar, and combinations thereof.

10. A method for reducing the incidence of infestation of a parasite on a companion animal and killing a parasite in combination, the method comprising topically applying to a companion animal a composition comprising active ingredients, wherein the active ingredients consist of methyl salicylate, thymol, vanillin, and lemon grass oil, and wherein the active ingredients are present in an amount of from about 10% to about 25% by weight.

11. A method for reducing the incidence of infestation of a parasite on a companion animal and killing a parasite in combination, the method comprising topically applying to a companion animal a composition comprising from about 2.5% to about 25% by weight of an active ingredient, wherein the active ingredient consists of methyl salicylate, thymol, vanillin, and lemon grass oil, from about 50% to about 80% by weight of an aqueous solvent, and from about 15% to about 35% by weight of a surfactant.

12. The method of claim 11, wherein the surfactant is selected from the group consisting of anionic, nonionic, amphoteric, zwitterionic surfactants, and combinations thereof.

13. The method of claim 11, wherein the composition further comprises from about 0.5% to about 3% by weight of a thickener, wherein the thickener is selected from the group consisting of water-soluble, guar- or xanthan-based gums, cellulose ethers, microcrystalline cellulose anti-packing agents, and combinations thereof.

14. The method of claim 11, wherein the composition further comprises from about 0.01% to about 1% by weight of a preservative, wherein the preservative is selected from the group consisting of sodium benzoate, parabens, Dimethylol Dimethyl hydantoin, Tetrasodium Ethylene Diamine Tetraacetate, chloroallyl hexaminium chloride, and combinations thereof.

15. A method for reducing the incidence of infestation of a parasite on a companion animal and killing a parasite in combination, the method comprising topically applying to a companion animal a spot-on composition comprising from about 10% to about 25% by weight of an active ingredient, wherein the active ingredient consists of methyl salicylate, thymol, vanillin, and lemon grass oil, and from about 75% to about 90% by weight of a solvent.

16. A method for reducing the incidence of infestation of a parasite on a companion animal and killing a parasite in combination, the method comprising topically applying to a companion animal a powder composition comprising from about 2.5% to about 10% by weight of an active ingredient, wherein the active ingredient consists of methyl salicylate, thymol, vanillin, and lemon grass oil, from about 40% to about 60% by weight of an absorbent, and from about 30% to about 50% by weight of a carrier.

17. A method for reducing the incidence of infestation of a parasite on a companion animal and killing a parasite in combination, the method comprising topically applying to a companion animal a spray on composition comprising from about 2.5% to about 20% by weight of an active ingredient, wherein the active ingredient consists of methyl salicylate, thymol, vanillin, and lemon grass oil, and from about 80% to about 99% by weight of a carrier.

18. A method for reducing the incidence of infestation of a parasite on a companion animal and killing a parasite in combination, the method comprising topically applying to a companion animal a shampoo composition comprising from about 10% to about 20% by weight of an active ingredient, wherein the active ingredient consists of methyl salicylate, thymol, vanillin, and lemon grass oil, and from about 50% to about 80% by weight of an aqueous solvent.

* * * * *